(12) United States Patent
Barrett

(10) Patent No.: US 8,945,221 B2
(45) Date of Patent: Feb. 3, 2015

(54) ANTERIOR LUMBAR INTERBODY GRAFT

(76) Inventor: Pat Barrett, Jackson, MS (US)

( * ) Notice: Subject to any disclaimer, the term of this patent is extended or adjusted under 35 U.S.C. 154(b) by 791 days.

(21) Appl. No.: 12/329,086

(22) Filed: Dec. 5, 2008

(65) Prior Publication Data

US 2009/0210058 A1  Aug. 20, 2009

Related U.S. Application Data

(60) Provisional application No. 60/992,428, filed on Dec. 5, 2007.

(51) Int. Cl.
*A61F 2/44* (2006.01)
*A61F 2/28* (2006.01)
*A61F 2/46* (2006.01)
*A61F 2/30* (2006.01)

(52) U.S. Cl.
CPC ........... *A61F 2/4465* (2013.01); *A61F 2/28* (2013.01); *A61F 2/4611* (2013.01); *A61F 2002/30062* (2013.01); *A61F 2002/302* (2013.01); *A61F 2002/30772* (2013.01); *A61F 2002/3082* (2013.01); *A61F 2002/3083* (2013.01); *A61F 2210/0004* (2013.01); *A61F 2230/0065* (2013.01); *A61F 2310/00017* (2013.01); *A61F 2310/00023* (2013.01); *A61F 2310/00359* (2013.01)
USPC ........................................ 623/17.11; 606/246

(58) Field of Classification Search
USPC .......... 623/11.11–17.19; 606/246, 279, 86 A, 606/914, 61
See application file for complete search history.

(56) References Cited

U.S. PATENT DOCUMENTS

| | | | | |
|---|---|---|---|---|
| 5,306,308 | A * | 4/1994 | Gross et al. | 623/17.16 |
| 7,303,583 | B1 * | 12/2007 | Schar et al. | 623/17.16 |
| 2002/0029084 | A1 * | 3/2002 | Paul et al. | 623/23.63 |
| 2002/0099443 | A1 * | 7/2002 | Messerli et al. | 623/17.11 |
| 2003/0100950 | A1 * | 5/2003 | Moret | 623/17.16 |
| 2008/0097610 | A1 * | 4/2008 | Guyer et al. | 623/17.16 |

* cited by examiner

*Primary Examiner* — Kevin T Truong
*Assistant Examiner* — Samuel Hanna
(74) *Attorney, Agent, or Firm* — Cermak Nakajima & McGowan; Adam Cermak

(57) ABSTRACT

An anterior lumbar interbody graft includes a wedge-shaped body including a hole and recesses formed in the top and bottom surfaces, radiating away from the hole.

2 Claims, 1 Drawing Sheet

ANTERIOR LUMBAR INTERBODY GRAFT

This application claims priority under 35 U.S.C. §119 to U.S. Provisional patent application No. 60/992,428, filed 5 Dec. 2007, the entirety of which is incorporated by reference herein.

BACKGROUND

1. Field of Endeavor

The present invention relates to devices and systems useful as anterior lumbar interbody grafts.

2. Brief Description of the Related Art

An interbody grafts are used in the lumbar spine. The grafts are placed by a surgeon between two vertebral bodies, to maintain disc height and keep vertebral bodies from collapsing. Currently, existing grafts on the market are two separate devices—Anterior and Anterior-Lateral grafts—which requires surgeons to stock both varieties, increasing costs. The market also includes Anterior Cage or Anterior Cervical Cage devices.

There remains a need for an interbody graft that can be used for multiple purposes.

SUMMARY

According to one of numerous aspects of the present invention, an anterior lumbar interbody graft comprises a wedge-shaped graft body having a top surface, a bottom surface, side surfaces extending between the top and bottom surfaces, first and second thicknesses of the graft body between the top and bottom surfaces at respective, opposite side surfaces of the graft body, the second thickness being less than the first thickness, a hole through the graft body between the top and bottom surfaces, and at least one recess formed in at least one of the top surface and the bottom surface.

Still other aspects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to exemplary embodiments of the apparatus and method, given only by way of example, and with reference to the accompanying drawings, in which.

DETAILED DESCRIPTION OF EXEMPLARY EMBODIMENTS

Figure 1:
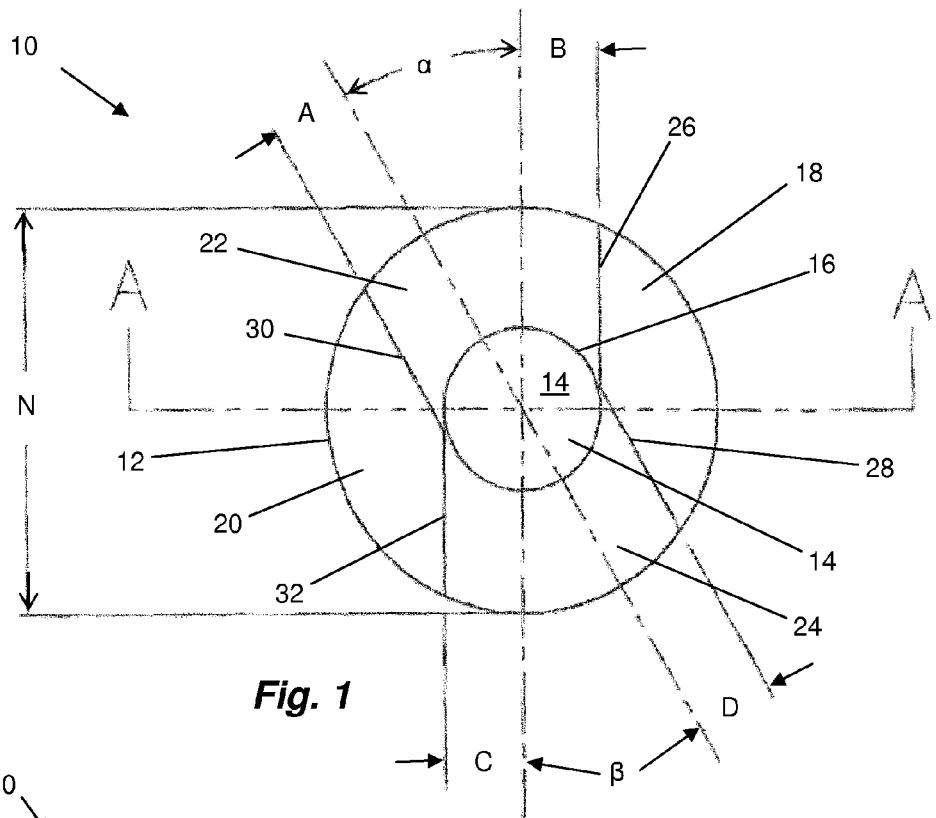
FIG. 1 illustrates a top plan view of a first exemplary graft embodying principles of the present invention.

Referring to the drawing figures, like reference numerals designate identical or corresponding elements throughout the several figures.

In general terms, an Anterior Lumbar Interbody Graft ("ALIG") includes a preferably round body that can be made out of titanium, stainless steel, bone, or a bioresorbable material. The ALIG can have various heights and diameters; exemplary, non-limiting examples are described elsewhere herein. The purpose of the ALIG is to provide a device that can be used both as an Anterior Lumbar Interbody Graft and Anterior-Lateral Lumbar Interbody Graft. An ALIG in accordance with principles of the present invention can reduce the number of different grafts that need to be stocked by a medical facility, because it has multiple uses.

An exemplary ALIG in accordance the present invention includes indentions or recesses formed in the top, bottom, or both surfaces, as suggested in the drawings. Preferably, although not necessarily, the recesses are formed at 0 degrees and 45 degrees, relative to the center hole of the ALIG, to allow the graft to be used as either an Anterior or Anterior-Lateral graft.

The angle(s) $\alpha$, $\beta$ at which the recesses radiate away from the center hole are preferably between about 15 degrees and 45 degrees, more preferably between about 25 degrees and about 35 degrees, yet further preferably about 30 degrees. While the figures illustrate four recesses, two on each of the top and bottom surfaces, extending away from the hole in generally opposite direction, fewer than all four recesses can be provided. The recesses preferably have widths that increase outwardly, as illustrated; alternatively, the recesses can have constant or decreasing widths. The graft body can be circular, as illustrated, or any of numerous other shapes, including trapezoidal.

The graft body device is preferably round. Optionally, the graft body can include teeth on the outer surfaces, e.g., the ends and/or top and bottom surfaces, to help with fixation in situ. An ALIG in accordance with the present invention is preferably, although not limited to, insertion into to the lumbar region of the spine from L2-S1, but is also insertable into the other portions of the lumbar region.

Turning now to the drawing figures, an exemplary embodiment of a graft 10 is illustrated. The graft 10 includes an outer sidewall 12, a hole 14, and an inner sidewall 16 delimiting the hole. Preferably, although not necessarily, the hole 14 is circular and located at the geometric center of the graft 10, although other shapes and positions of the hole also adhere to principles of the present invention. The graft 10 is advantageously, yet not necessarily, symmetrical with respect to a lateral plane extending through the sidewalls 12, 16, and the hole 14.

The graft 10 includes at least one, and preferably two, upper surfaces, including a first upper surface 18 and a second upper surface 20, located on diametrically opposite sides of the hole 14. Similarly, the graft 10 includes first and second lower surfaces 34, 36 (see FIG. 2), opposite each other. The upper surfaces 18, 20, extend from the outer sidewall 12 laterally inward and terminate at upstanding inner walls 26, 28, 30, 32. While walls 26-32 are illustrated being orthogonal to the upper surfaces, they can be formed at non-right angles. One or more of the outer surfaces can include teeth 40.

The graft 10 advantageously includes lower surfaces 22, 24, on the upper face of the graft, which are recessed from the upper surfaces 18, 20. Advantageously, yet not necessarily, the graft also includes similar recessed surfaces formed in the lower face of the graft (see FIG. 2). The lower surfaces 22, 24 are laterally delimited by the walls 26-32, and therefore define two recesses in the top surface of the graft 10. The walls 26-32 preferably extend from a point at or adjacent to the sidewall 16 (i.e., the hole 14) to the outer sidewall 12 at angles $\alpha$ (alpha) and $\beta$ (beta). The angle $\alpha$, $\beta$ at which the walls, and therefore the recesses, radiate away from the hole 14 are preferably between about 15 degrees and 45 degrees, more preferably between about 25 degrees and about 35 degrees, yet further preferably about 30 degrees. Further optionally, the angles $\alpha$, $\beta$ can be the same or different, that is, the walls 26-32 can form different angles delimiting the lower surfaces.

Figure 2:
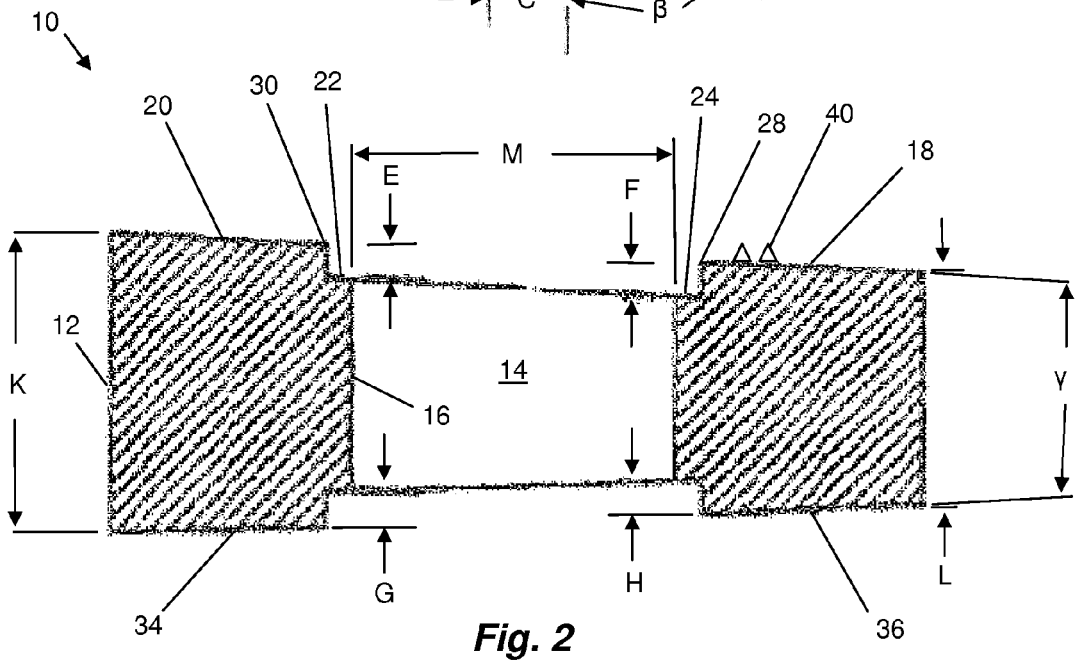
FIG. 2 illustrates a cross-sectional illustration, taken at line A-A, in FIG. 1.

With reference to FIG. 2, the graft 10 is also advantageously, yet optionally, formed in a wedge shape at a lordosis angle γ (gamma). The angle γ can between about 1 degree and about 17 degrees, preferably between about 3 degrees and about 11 degrees, and more preferably about 7 degrees.

FIGS. 1 and 2 also indicate dimensions of one exemplary embodiment of a graft 10. Preferably, although not necessarily:

A=B=C=D, and are 5.00 mm
E=F=G=H, and are 1.00 mm
K (anterior side)=9.00 mm (at the widest portion of the wall 12)
L (posterior side)=7.00 mm (at the narrowest portion of the wall 12)
M=10.00 mm
N=25.00 mm In use, a surgeon can implant the graft 10 for as either an anterior interbody graft or as an anterior-lateral interbody graft, using the implantation methods already known by those of ordinary skill in the art.

While the invention has been described in detail with reference to exemplary embodiments thereof, it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. An anterior lumbar interbody graft comprising: a cylindrical, wedge-shaped, single-piece, unitary graft body having a top surface, a bottom surface, side surfaces extending between the top and bottom surfaces, first and second thicknesses of the graft body between the top and bottom surfaces at respective, opposite side surfaces of the graft body, the second thickness being less than the first thickness; a hole through the graft body between the top and bottom surfaces, the hole having a diameter; and two recesses formed in both the top surface and in the bottom surface, the two top surface recesses extending in opposite directions from the hole to corresponding opposite side surfaces of the side surfaces extending between the top and bottom surfaces, and the two bottom surface recesses extending in opposite directions from the hole to corresponding opposite side surfaces of the side surfaces extending between the top and bottom surfaces; wherein each recess of the two top surface recesses and the two bottom surface recesses comprises a first width adjacent to the hole having the same size as the hole diameter, and a second width at the corresponding side surface remote from the hole being larger than the first width.

2. The anterior lumbar interbody graft according to claim 1, further comprising:

teeth formed in at least one of the top surface and the bottom surface, configured and arranged to assist fixing the body in place when inserted between two vertebral bodies.

* * * * *